(12) United States Patent
Cao et al.

(10) Patent No.: US 11,105,811 B2
(45) Date of Patent: Aug. 31, 2021

(54) PREPARATION METHOD AND SECONDARY DISPERSION OF MONODISPERSE AMINATED MANODIAMOND COLLOID SOLUTION AND ITS APPLICATION IN CELLULAR BIOMARKING

(71) Applicant: Central China Normal University, Wuhan (CN)

(72) Inventors: Yu Cao, Wuhan (CN); Mingxin Fang, Wuhan (CN); Xiaojuan Cai, Wuhan (CN); Shurui Shi, Wuhan (CN); Cui Liu, Wuhan (CN)

(73) Assignee: Central China Normal University, Wuhan (CN)

( * ) Notice: Subject to any disclaimer, the term of this patent is extended or adjusted under 35 U.S.C. 154(b) by 0 days.

(21) Appl. No.: 17/117,173

(22) Filed: Dec. 10, 2020

(65) Prior Publication Data

US 2021/0088527 A1 Mar. 25, 2021

Related U.S. Application Data

(63) Continuation of application No. PCT/CN2018/110699, filed on Oct. 17, 2018.

(51) Int. Cl.
*C01B 32/28* (2017.01)
*G01N 33/58* (2006.01)
(Continued)

(52) U.S. Cl.
CPC ........ *G01N 33/587* (2013.01); *B01J 13/0008* (2013.01); *C01B 32/28* (2017.08);
(Continued)

(58) Field of Classification Search
CPC ............ G01N 33/587; G01N 21/6428; G01N 2021/6439; C01B 32/28; B01J 13/0008;
(Continued)

(56) References Cited

U.S. PATENT DOCUMENTS

2018/0134563 A1* 5/2018 Mochalin ................ B02C 23/06

FOREIGN PATENT DOCUMENTS

| CN | 103173267 A | 6/2013 |
|---|---|---|
| CN | 104261404 A | 9/2014 |

(Continued)

OTHER PUBLICATIONS

Turcheniuk, Kostiantyn, and V. N. Mochalin. "Adsorption behavior and reduction of copper (II) acetate on the surface of detonation nanodiamond with well defined surface chemistry." Carbon 109 (2016): 98-105.*

(Continued)

*Primary Examiner* — Richard M Rump
(74) *Attorney, Agent, or Firm* — Avi Avraham Jencmen

(57) ABSTRACT

A preparation method and secondary dispersion of monodisperse aminated Nanodiamond colloid solution and its application in cellular biomarking are provided. Preparation method comprise: mixing purified Nanodiamond powder with ammonium chloride and sodium chloride, placing the mixture in a ball mill for dry ball milling, washing the ball-milled mixture with deionized water, and performing ultrasonic dispersion and centrifuging to obtain the monodispersed aminated Nanodiamond colloid solution. Secondary dispersion process comprising: drying aminated Nanodiamond colloid solution to obtain aminated Nanodiamond powder, re-dispersing the powder in DMSO (dimethyl sulphoxide), deionized water, ethanol, DMF (dimethylformamide) or other solvents with ultrasonic or shearing processing. The aminated Nanodiamond has high yield and good monodispersity. The preparation method is simple to operate, no special requirements on reaction equipment, no inert gas atmosphere is required in the whole reaction process and it is easy to be industrialized. The aminated Nanodiamond can be applied to cellular biomarking.

5 Claims, 10 Drawing Sheets

(51) Int. Cl.
*B01J 13/00* (2006.01)
*G01N 21/64* (2006.01)

(52) U.S. Cl.
CPC ...... *G01N 21/6428* (2013.01); *C01P 2002/72* (2013.01); *C01P 2004/04* (2013.01); *C01P 2004/61* (2013.01); *C01P 2004/62* (2013.01); *C01P 2004/64* (2013.01); *C01P 2006/90* (2013.01); *G01N 2021/6439* (2013.01)

(58) Field of Classification Search
CPC .............. C01P 2004/61; C01P 2004/64; C01P 2004/04; C01P 2002/72; C01P 2004/62; C01P 2006/90
See application file for complete search history.

(56) References Cited

FOREIGN PATENT DOCUMENTS

| | | |
|---|---|---|
| CN | 104261385 A | 1/2015 |
| CN | 105153942 A | 12/2015 |
| CN | 105452164 A | 3/2016 |
| CN | 108251058 A | 7/2018 |

OTHER PUBLICATIONS

Zhang, Wangxi, et al. "Review on the Development of Nanodiamonds Used as Functional Materials". vol. 32 Issue: 7 pp. 2183-2188 (2018).*
Kanyuk, M. I. "Use of nanodiamonds in biomedicine." Biotechnologia Acta 8.2 (2015).*
"Dispersion behavior and the influences of ball milling technique on functionalization of detonated nano-diamonds", Muhammad Khan et al.Diamond & Related Materials, 61, 32-40.

* cited by examiner

PREPARATION METHOD AND SECONDARY DISPERSION OF MONODISPERSE AMINATED MANODIAMOND COLLOID SOLUTION AND ITS APPLICATION IN CELLULAR BIOMARKING

CROSS-REFERENCE TO RELATED APPLICATIONS

The application claims priority to Chinese patent application No. 201811010729.1, filed on Aug. 31, 2018, the entire contents of which are incorporated herein by reference.

TECHNICAL FIELD

The present disclosure relates to the technical field of Nanodiamond processing, and more particularly to a preparation method and secondary dispersion of monodisperse aminated Nanodiamond colloid solution and its application in cellular biomarking.

BACKGROUND

With unique characteristics such as semiconductor properties and biocompatibility, Nanodiamonds are widely used as base material for biosensors. Because of its unique chemical composition and electrical properties, Nanodiamonds are more conducive to the development of bioelectronics and biosensors compared to other traditional materials, such as gold, silicon, and glass. Functionalization of Nanodiamonds is an important technique that makes them suitable for biomedical applications. Since biomolecules are generally composed of amino acid sequences, many researchers have noticed that perhaps amino-functionalized Nanodiamonds can be well applied to biosensors.

Now-a-days, a lot of research has been focused on the functionalization of Nanodiamonds. The China patent application CN 103173267 A provided a nano diamond derivative with end group as amino group as well as preparation method and application thereof. The derivative was prepared according to the following steps: firstly, Nanodiamonds purified and oxidized by mixed acid were used to react with thionyl chloride; then it was reacted with diamine compound and trichloro-triazine for nucleophilic substitution; and then, reacted iteratively with diamine compounds and trichloro-s-triazine, thus derivatives were obtained. However, the preparation process is complicated, the reaction conditions are harsh, and the nucleophilic substitution reaction must be performed with the protection of inert gas, the production cost is high, and the product contains lots of impurities. In addition, in M. Khan's work (M. Khan, N. Shahzad, et al. Dispersion behavior and the influences of ball milling technique on functionalization of detonated nano-diamonds[J]. Diamond & Related Materials 61 (2016) 32-40.), ball milling has been performed with different milling media ($NH_4HCO_3$, NaCl and sucrose) and investigate the effect of different milling media on detonated Nanodiamonds deaggregation followed by its dispersion behavior in different solvents (ethanol, deionized water and dimethyl sulphoxide (DMSO)). However, the aminated Nanodiamond produced by M. Khan still has the same problem of impurities. Although the aminated Nanodiamond assisted by the grinding media has better dispersibility in epoxy resin, monodisperse Nanodiamond colloid cannot be obtained.

This application is proposed based on the above technical problems existing in the prior art.

SUMMARY

In view of the above problems in the prior art, the present disclosure provides a preparation method and secondary dispersion of monodisperse aminated Nanodiamond colloid solution and its application in cellular biomarking. The purpose of it is to make the surface of Nanodiamond modified by amination, and the obtained monodisperse colloid solution can be dispersed again.

In order to achieve the above-mentioned first objective, the technical scheme of the present disclosure is described as follows.

A method for preparing a monodisperse aminated Nanodiamond colloid solution, comprises steps of: mixing a purified Nanodiamond powder of appropriate particle size with ammonium chloride and sodium chloride in a reasonable mass ratio at room temperature, placing in a ball mill for dry ball milling, washing with deionized water, dispersing with ultrasonic, and centrifuging to obtain monodisperse amine Nanodiamond black colloid solution.

The purified Nanodiamond powder in the above-mentioned technical scheme of the present disclosure can be commodity sold in the market, or be purified detonated Nanodiamonds. Preferably, a purity of the purified Nanodiamond powder is higher than 90%, and it is better if the purity is higher than 95%; the particle size of the purified Nanodiamond powder is in a range of 30 nm-100 μm.

Preferably, the mass ratio of the purified Nanodiamond to deionized water is in a range of 1:(20-2000), the mass ratio of ammonium chloride and sodium chloride is in a range of 1:(2-100).

Preferably, the mass ratio of the purified Nanodiamond powder to the ammonium chloride is in a range of 1:(0.1-100).

Preferably, adding ball milling beads in the ball milling process, the ball milling beads are non-metallic ball milling beads, including but not limited to agate, corundum, zirconia, and silica, agate is better.

Preferably, a diameter of the ball milling beads is longer than 1 mm, preferably longer than 4 mm. The ball milling beads can be with a single diameter, or be composed of a mixture of ball milling beads with different diameters. If it is composed of a mixture of ball milled beads with different diameters, a bead diameter ratio is in a range of 1.5-200, more preferably in a range of 2-10.

Preferably, an efficient planetary ball mill is used for ball milling at room temperature, a linear rotational speed is 20-600 r/min, a linear speed is 20-600 m/min, and a ball milling time is in a range of 0.1-20 h.

Preferably, the linear rotational speed is 512 r/min. During an optimization process, we also found that the amount of ammonium chloride also has significant impact on the amino content of the final product. The smaller or larger the quality of ammonium chloride, the less amino content on the surface of the Nanodiamond obtained.

Preferably, the ratio of amination reagent (the mass ratio of Nanodiamond and ammonium chloride) is 1:0, 1:5, 1:10, 1:15, or 1:20. While the ratio of amination reagent is relatively small, the concentration of ammonium chloride decomposed by the amination reagent in the system is smaller, and the amination modification is insufficient. While the ratio of amination reagent is relatively large, the concentration of the decomposed amino group is larger, which makes the amination reaction balance earlier and reduces the amino group concentration.

In order to realize a re-dispersion of aminated Nanodiamond colloid solution, comprises steps of:

(i) drying the aminated Nanodiamond black colloid solution prepared by the method to obtain aminated Nanodiamond powder;

(ii) dispersing the aminated Nanodiamond powder prepared in step (i) in solvent once again with an ultrasonic or shearing processing, shaking to obtain clear and transparent black colloid solution.

Preferably, the drying process in step (i) comprise any one of rotary evaporator drying, spray drying or freeze drying.

Preferably, the drying temperature of the rotary evaporator in step (i) is not higher than 80° C., which can be 60° C., 65° C., 70° C. or 80° C., and generally does not exceed 80° C.

Preferably, the solvent in step (ii) comprise at least one of deionized water, dimethyl sulfoxide (DMSO), ethanol, ethylene glycol, or dimethylformamide (DMF), or other composite solvents containing any of the above solvents with a volume ratio over 20%.

Preferably, in step (ii), an ultrasonic cleaner with the power of 100-1000 W can be used, shear dispersion (>500 rpm) processing time is 15 minutes.

The disclosure also discloses the application of aminated nano diamond, such as use of aminated Nanodiamonds as fluorescent probes in cellular biomarking.

Preferably, a concentration of aminated Nanodiamonds as fluorescent probes to label cells is in a range of 0.5-2 mg/ml.

Compared with the prior art, the beneficial technical effects of the preparation method and secondary dispersion technology of monodisperse aminated Nanodiamond colloid solution and application of the aminated Nanodiamond to cellular biomarking are described as follows.

(1) The preparation method provided by the present disclosure is simple to operate, simple in process, no special requirements on reaction equipment, no inert gas atmosphere is required in the whole reaction process, the reagents are cheap, it is easy to be industrialized.

(2) The yield of the aminated Nanodiamond prepared by the ball milling method is higher than 90%, reaching 97%, and the prepared aminated Nanodiamond colloid has monodisperse properties.

(3) The aminated Nanodiamond powder obtained by the disclosure can be dispersed twice, which makes a transportation of the dispersed Nanodiamond more convenient, and broadens the application field of the Nanodiamond.

(4) No adverse effects on the environment during the experiment of the present disclosure, the acid waste liquid treatment method is relatively simple, and can be further concentrated or recycled

DETAILED DESCRIPTION OF THE EMBODIMENTS

In order to make objects, technical solutions and advantages of the present disclosure clearer, the present disclosure is further described in detail with examples. The devices and reagents used in the examples are commercially available unless otherwise noted.

The examples are only for explaining the present disclosure, not for limiting the present disclosure, since various modifications and substitutions can be made without departing from the present disclosure. As such, further modifications and equivalents of the present disclosure herein disclosed may occur to persons having ordinary skills in the art using no more than routine experimentation.

For the present disclosure to be better understood and not limited by scope, all numbers in this application that express amounts, percentages, and other values should be understood as modified by the word "about" in all cases. Therefore, unless otherwise specified, the numerical parameters listed in the specification and the appended claims are approximate values, which may be changed according to the desired properties that are attempted to be obtained. Each numerical parameter should at least be regarded as obtained based on the reported significant figures and through conventional rounding methods.

In order to increase the yield of aminated Nanodiamonds, the Nanodiamonds in the following examples are all purified, and the process flow are described as follows.

10 g Nanodiamond gray powder is used to mix with 30 g~50 g concentrated sulfuric acid and 10 g potassium permanganate in a reactor, 220° C. for 8 h. Nanodiamond gray powder is oxidized and purified in concentrated sulfuric acid medium by potassium permanganate in high temperature environment. After that, it is continuously cleaned with deionized water by ultrasonic to neutrality. Purified Nanodiamond powder is isolated by centrifugation and drying. A diamond content in Nanodiamond gray powder is greater than 90%; a mass fraction of concentrated sulfuric acid is 98%, both of which can be purchased in commercial.

Example 1

In this example, a preparation method of monodisperse aminated Nanodiamond colloid solution are described as follows.

(1) Ball milling beads (a large agate bead diameter of 6.8 mm and a small bead diameter of 4.2 mm, mass ratio of 1:5) were put into a ball milling tank with the volume of 100 ml, to mix with 0.5 g purified Nanodiamond and 2.5 g chlorinated Sodium, no ammonium chloride. The ball mill (model: QM-1SP2, Nanjing University Instrument Factory) with a linear speed of 512 m/min works for 2 h. Take off the ball mill tank after turning off the ball mill for 30 minutes.

Figure 4:
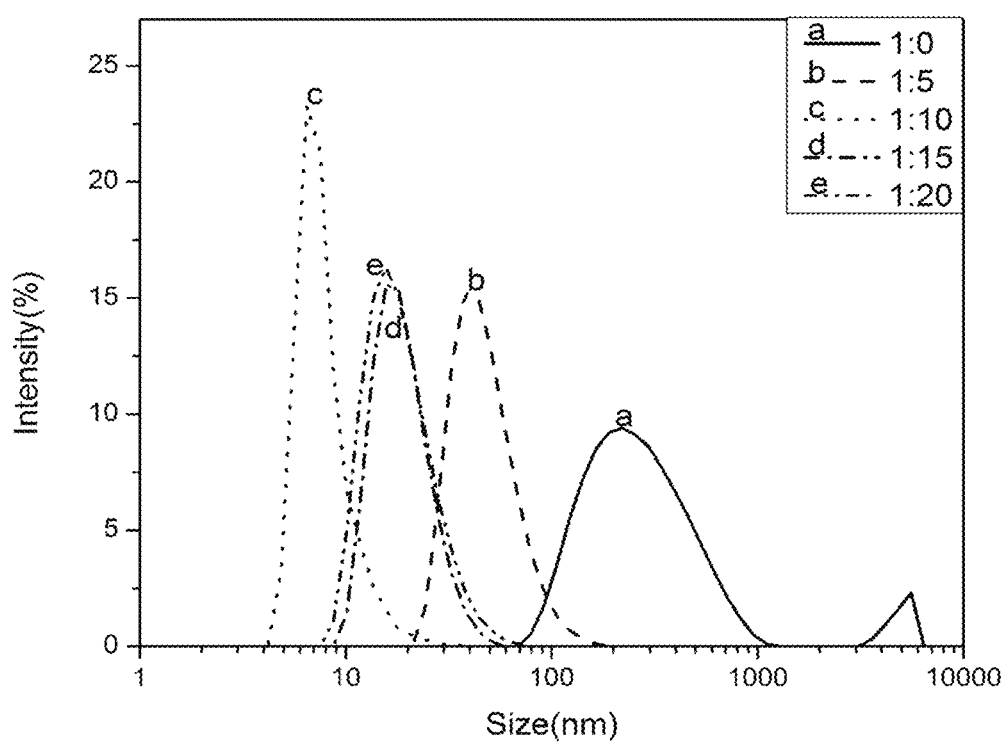
FIG. 4 shows a particle size distribution of Nanodiamond colloid solution in different amination reagent ratio conditions of example 1 to 5.

(2) The ball milling beads in the ball milling tank were washed with deionized water (250~300 ml, the volume of deionized water can be appropriately increased), and dispersed with ultrasonic (8000 W ultrasound generally did not exceed 1 min, 360 W ultrasound generally 15 min), and then centrifuged for 5 min with a speed of 10000 r/min, repeating 4 to 5 times to obtain clear and transparent monodisperse aminated Nanodiamond black colloid solution, which was characterized by dynamic light scattering (DLS), and the results were shown in FIG. 4.

In this example, a secondary dispersion technology of monodisperse aminated-Nanodiamond colloid solution are described as follows.

(1) Water solvent in the clear and transparent Nanodiamond black colloid solution was removed with a rotary evaporator (model: N-1001, Shanghai Ailang Instrument Co., Ltd.), and the temperature of water bath (model: SB-2000, Shanghai Ailang Instrument Co., Ltd.) was 80° C. In this way, aminated Nanodiamond powder was obtained.

Figure 7:
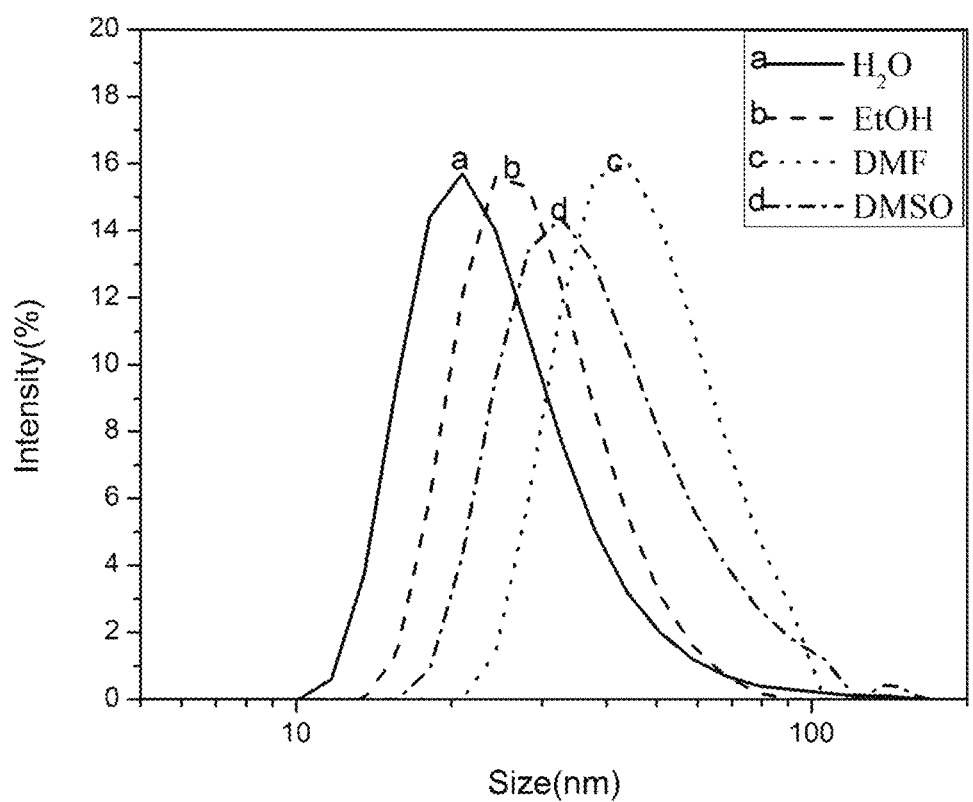
FIG. 7 shows a particle size distribution of colloid solution of aminated Nanodiamond prepared in example 3 for secondary dispersion in different solvents.

(2) The aminated Nanodiamond powder was dissolved in DMF by ultrasonic for 15 minutes to obtain clear and transparent black colloid solution of Nanodiamond with higher concentration, which was characterized by dynamic light scattering, and the result was shown in FIG. 7. The median size of the aminated Nanodiamonds in the colloid solution prepared in this example was about 50 nm, and the average particle size of the aminated Nanodiamonds in the colloid solution obtained by the secondary dispersion was about 60 nm.

Example 2

In this example, a preparation method of monodisperse aminated Nanodiamond colloid solution are described as follows.

(1) The ball milling beads (a large agate bead diameter of 6.8 mm and a small bead diameter of 4.2 mm, mass ratio of 1:5) were put into a ball milling tank with the volume of 100 ml, to mix with 0.5 g purified Nanodiamond and 2.5 g chlorinated Sodium, 2.5 g ammonium chloride. The ball mill (model: QM-1SP2, Nanjing University Instrument Factory) with a linear speed of 512 m/min works for 2 h. Take off the ball mill tank after turning off the ball mill for 30 minutes.

Figure 8:
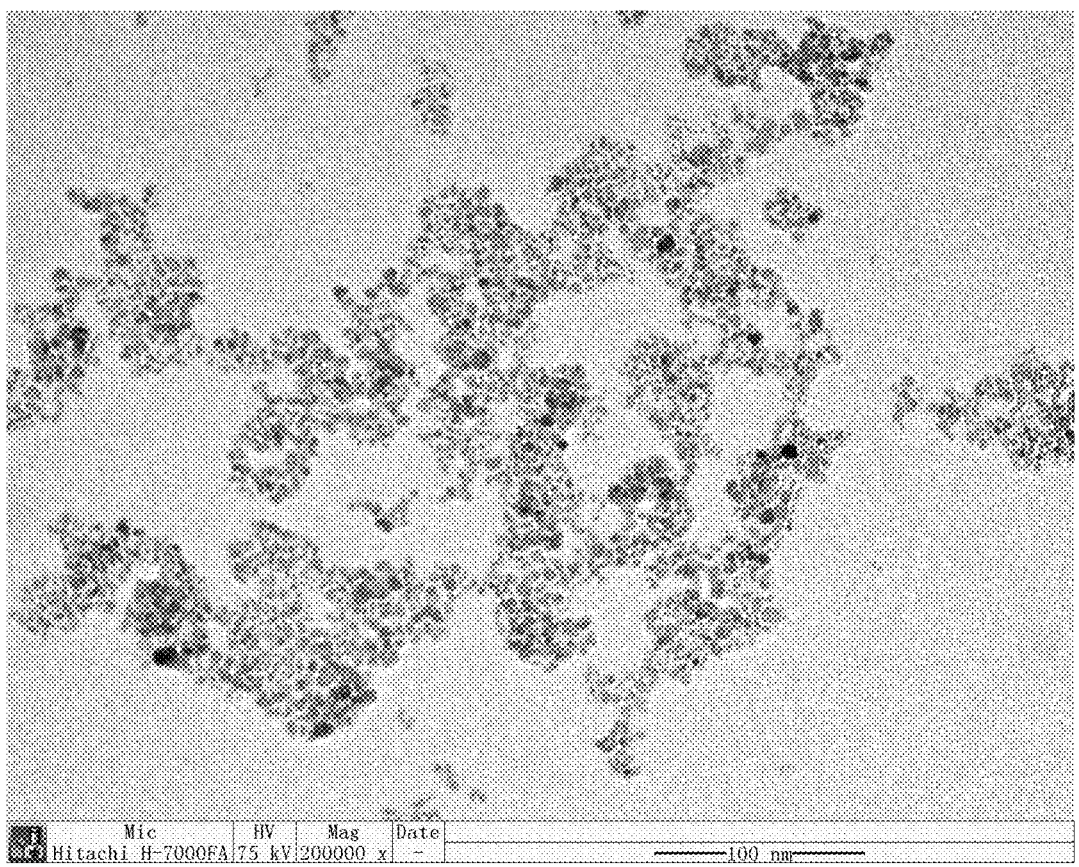
FIG. 8 shows a TEM images of aminated Nanodiamond prepared in example 3.
Figure 9A:
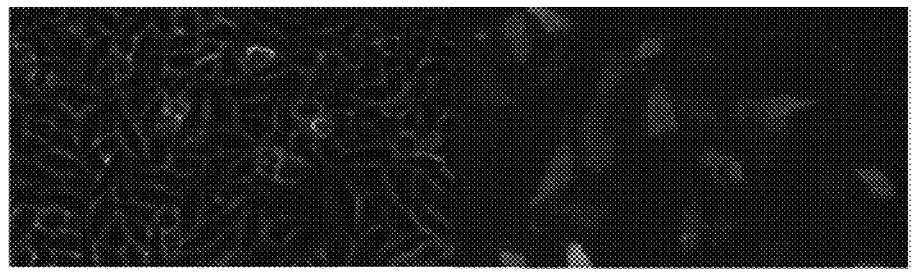
FIG. 9A HepG2, FIG. 9B HeLa, FIG. 9C L02, FIG. 9D H3B, FIG. 9E NIH 3T3; a bright field picture is on the left, and a fluorescence field picture is on the right.
Figure 9B:
FIG. 9 shows the images of different cells cultured in aminated Nanodiamond mixture for 30 minutes.
Figure 9C:
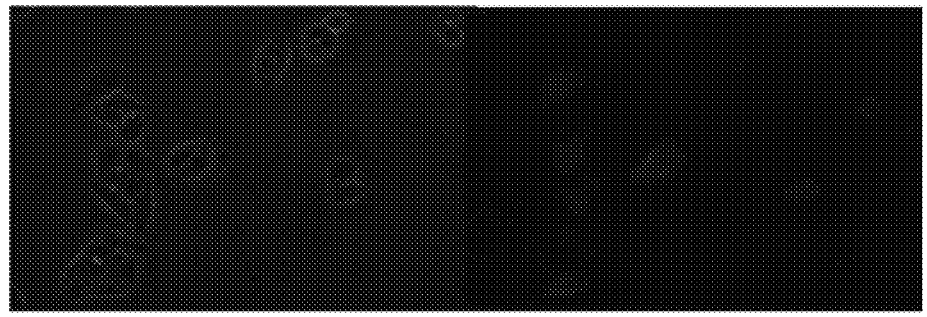
Figure 9D:
Figure 9E:
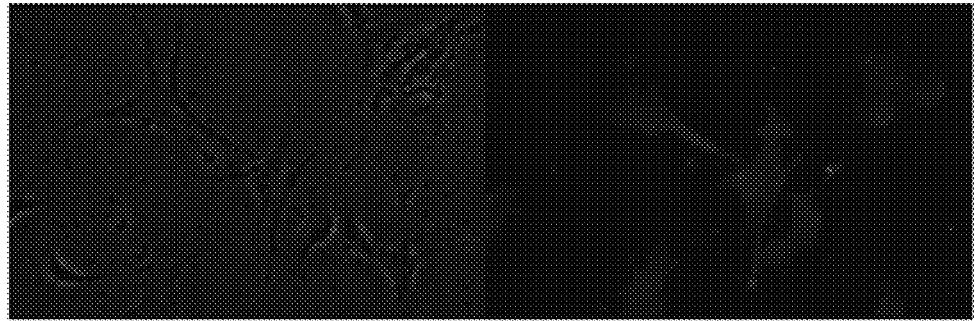

(2) The ball milling beads in the ball milling tank were washed with deionized water (250~300 ml, the volume of deionized water can be appropriately increased), and dispersed with ultrasonic (8000 W ultrasound generally did not exceed 1 min, 360 W ultrasound generally 15 min), and then centrifuged for 5 min with a speed of 10000 r/min, repeating 4 to 5 times to obtain clear and transparent monodisperse aminated Nanodiamond black colloid solution, which was characterized by dynamic light scattering (DLS), and the results were shown in FIG. 4; analyzed by transmission electron microscope, and its morphology was shown in FIG. 8.

In this example, a secondary dispersion technology of a monodisperse aminated Nanodiamond colloid solution are described as follows.

(1) Water solvent in the clear and transparent Nanodiamond black colloid solution was removed with a rotary evaporator (model: N-1001, Shanghai Ailang Instrument Co., Ltd.), and the temperature of the water bath (model: SB-2000, Shanghai Ailang Instrument Co., Ltd.) was 80° C. In this way, aminated Nanodiamond powder was obtained. The yield of Nanodiamond after amination modification cab be calculated using the following Eq.

$$Yield = m_1/m_0 \times 100\%$$

Where, $m_0$—the mass of Nanodiamond raw material, in g; $m_1$—the mass of aminated nanodiamond after drying, in g;

In this example, the mass of the dispersed Nanodiamond after amination modification was 0.473 g, and the yield was 94.6%.

(2) The aminated Nanodiamond powder was dissolved in deionized water by ultrasonic for 15 minutes to obtain clear and transparent black colloid solution of Nanodiamond with higher concentration, which was characterized by dynamic light scattering, and the result was shown in FIG. 7. The median size of the aminated Nanodiamonds in the colloid solution prepared in this example was about 50 nm, and the average particle size of the aminated Nanodiamonds in the colloid solution obtained by the secondary dispersion was about 50 nm.

Example 3

In this example, a preparation method of monodisperse aminated Nanodiamond colloid solution are described as follows.

(1) The ball milling beads (a large agate bead diameter of 6.8 mm and a small bead diameter of 4.2 mm, mass ratio of 1:5) were put into a ball milling tank with the volume of 100 ml, to mix with 0.5 g purified Nanodiamond and 2.5 g chlorinated Sodium, 5 g ammonium chloride. The ball mill (model: QM-1SP2, Nanjing University Instrument Factory) with a linear speed of 512 m/min works for 2 h. Take off the ball mill tank after turning off the ball mill for 30 minutes.

(2) The ball milling beads in the ball milling tank were washed with deionized water (250~300 ml, the volume of deionized water can be appropriately increased), and dispersed with ultrasonic (8000 W ultrasound generally does not exceed 1 min, 360 W ultrasound generally 15 min), and then centrifuged for 5 min with a speed of 10000 r/min, repeating 4 to 5 times to obtain clear and transparent monodisperse aminated Nanodiamond black colloid solution, which was characterized by dynamic light scattering (DLS), and the results were shown in FIG. 4.

In this example, a secondary dispersion technology of monodisperse aminated-Nanodiamond colloid solution are described as follows.

(1) Water solvent in the clear and transparent Nanodiamond black colloid solution was removed with a rotary evaporator (model: N-1001, Shanghai Ailang Instrument Co., Ltd.), and the temperature of water bath (model: SB-2000, Shanghai Ailang Instrument Co., Ltd.) was 80° C. In this way, aminated Nanodiamond powder was obtained.

(2) The aminated Nanodiamond powder was dissolved in DMSO by ultrasonic for 15 minutes to obtain clear and transparent black colloid solution of Nanodiamond with higher concentration.

The aminated Nanodiamond powder was tested by XRD. The test result was shown in FIG. 1. The XRD diffraction peaks of the aminated Nanodiamond powder and the Nanodiamond raw material and purified Nanodiamond were basically the same, which proved that the structure of the Nanodiamond after amination modification was basically unchanged.

The colloid solution after secondary dispersion was characterized by dynamic light scattering, and the result was shown in FIG. 7. The median size of the aminated Nanodiamonds in the colloid solution prepared in this example was about 50 nm, and the average particle size of the aminated Nanodiamonds in the colloid solution obtained by the secondary dispersion was about 60 nm.

Example 4

In this example, a preparation method of monodisperse aminated Nanodiamond colloid solution are described as follows.

(1) The ball milling beads (a large agate bead diameter of 6.8 mm and a small bead diameter of 4.2 mm, mass ratio of 1:5) were put into a ball milling tank with the volume of 100 ml, to mix with 0.5 g purified Nanodiamond and 2.5 g chlorinated Sodium, 7.5 g ammonium chloride. The ball mill (model: QM-1SP2, Nanjing University Instrument Factory) with a linear speed of 512 m/min works for 2 h. Take off the ball mill tank after turning off the ball mill for 30 minutes.

(2) The ball milling beads in the ball milling tank were washed with deionized water (250~300 ml, the volume of deionized water can be appropriately increased), and dispersed with ultrasonic (8000 W ultrasound generally did not exceed 1 min, 360 W ultrasound generally 15 min), and then centrifuged for 5 min with a speed of 10000 r/min, repeating 4 to 5 times to obtain clear and transparent monodisperse aminated Nanodiamond black colloid solution, which was characterized by dynamic light scattering (DLS), and the results were shown in FIG. 4.

In this example, a secondary dispersion technology of monodisperse aminated-Nanodiamond colloid solution are described as follows.

(1) Water solvent in the clear and transparent Nanodiamond black colloid solution was removed with a rotary evaporator (model: N-1001, Shanghai Ailang Instrument Co., Ltd.), and the temperature of water bath (model: SB-2000, Shanghai Ailang Instrument Co., Ltd.) was 80° C. In this way, aminated Nanodiamond powder was obtained.

(2) The aminated Nanodiamond powder was dissolved in ethanol by ultrasonic for 15 minutes to obtain clear and transparent black colloid solution of Nanodiamond with higher concentration, which was characterized by dynamic light scattering, and the result was shown in FIG. 7. The median size of the aminated Nanodiamonds in the colloid solution prepared in this example was about 50 nm, and the average particle size of the aminated Nanodiamonds in the colloid solution obtained by the secondary dispersion was about 60 nm.

Example 5

In this example, a preparation method of monodisperse aminated Nanodiamond colloid solution are described as follows.

(1) The ball milling beads (a large agate bead diameter of 6.8 mm and a small bead diameter of 4.2 mm, mass ratio of 1:5) were put into a ball milling tank with the volume of 100 ml, to mix with 0.5 g purified Nanodiamond and 2.5 g chlorinated Sodium, 10.0 g ammonium chloride. The ball mill (model: QM-1SP2, Nanjing University Instrument Factory) with a linear speed of 512 m/min works for 2 h. Take off the ball mill tank after turning off the ball mill for 30 minutes.

(2) The ball milling beads in the ball milling tank were washed with deionized water (250~300 ml, the volume of deionized water can be appropriately increased), and dispersed with ultrasonic (8000 W ultrasound generally did not exceed 1 min, 360 W ultrasound generally 15 min), and then centrifuged for 5 min with a speed of 10000 r/min, repeating 4 to 5 times to obtain clear and transparent monodisperse aminated Nanodiamond black colloid solution, which was characterized by dynamic light scattering (DLS), and the results were shown in FIG. 4.

In this example, a secondary dispersion technology of monodisperse aminated-Nanodiamond colloid solution are described as follows.

(1) Water solvent in the clear and transparent Nanodiamond black colloid solution was removed with a rotary evaporator (model: N-1001, Shanghai Ailang Instrument Co., Ltd.), and the temperature of water bath (model: SB-2000, Shanghai Ailang Instrument Co., Ltd.) was 80° C. In this way, aminated Nanodiamond powder was obtained.

(2) The aminated Nanodiamond powder was dissolved in ethanol by ultrasonic for 15 minutes to obtain clear and transparent black colloid solution of Nanodiamond with higher concentration.

Figure 1:
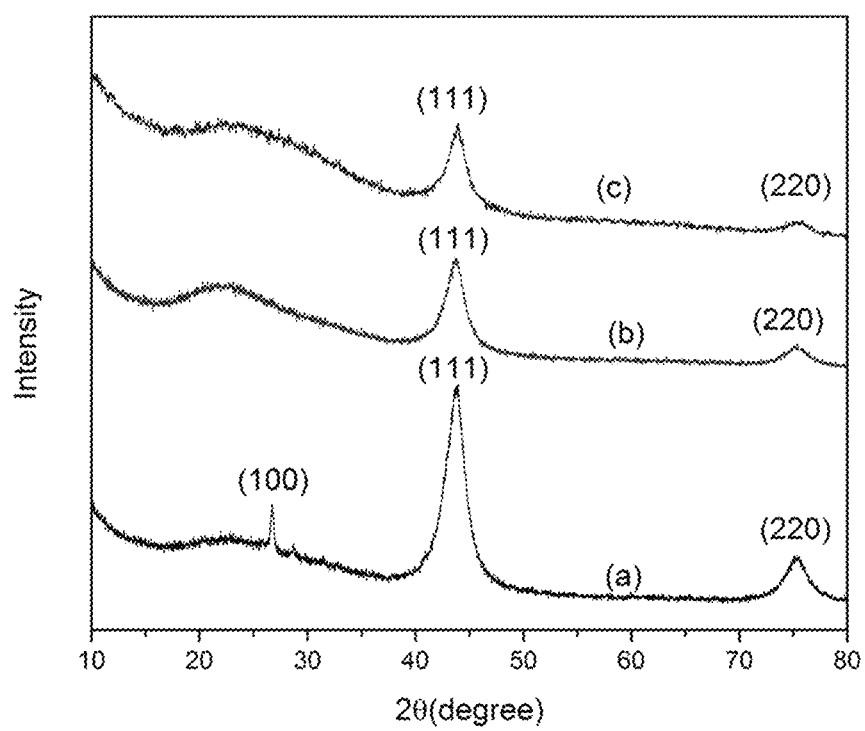
FIG. 1 shows a XRD patterns of Nanodiamond raw material (a), purified Nanodiamond (b), and aminated Nanodiamond (c) of example 3.

FIG. 1 shows a XRD patterns of Nanodiamond gray powder and purified Nanodiamond. From the XRD patterns of unpurified raw material of Nanodiamond, it can be observed that the peak at 20~30° degree appearing in (a) is showing a peak of impurities, such as graphite (100) and amorphous carbon, etc., and the noise is relatively high. This shows that the unpurified Nanodiamond crystal form is defective and contains certain content of non-diamond carbon. From the XRD patterns of Nanodiamond oxidized by potassium permanganate (b), it can be observed that the peak at 20~30° degree is disappeared, indicating that potassium permanganate has good impurity removal effect on amorphous carbon and graphite. Nanodiamond powder with high purity and perfect crystal shape is obtained through oxidation treatment. In addition, due to the strong oxidation of potassium permanganate, Nanodiamonds are etched, which reduces the carbon content of (111) and (220) crystal forms. From the XRD patterns of Nanodiamond modified by ball milling and amination in example 1 (c), it can be observed that the (111) crystal face and (220) crystal face of the nanodiamond modified by amination are complete, and the strength does not change much from that of the purified Nanodiamond. This shows that ball mill amination modification has no significant effect on the Nanodiamond crystal form, and the integrity of the Nanodiamond crystal form is maintained in the amination process.

Figure 2:
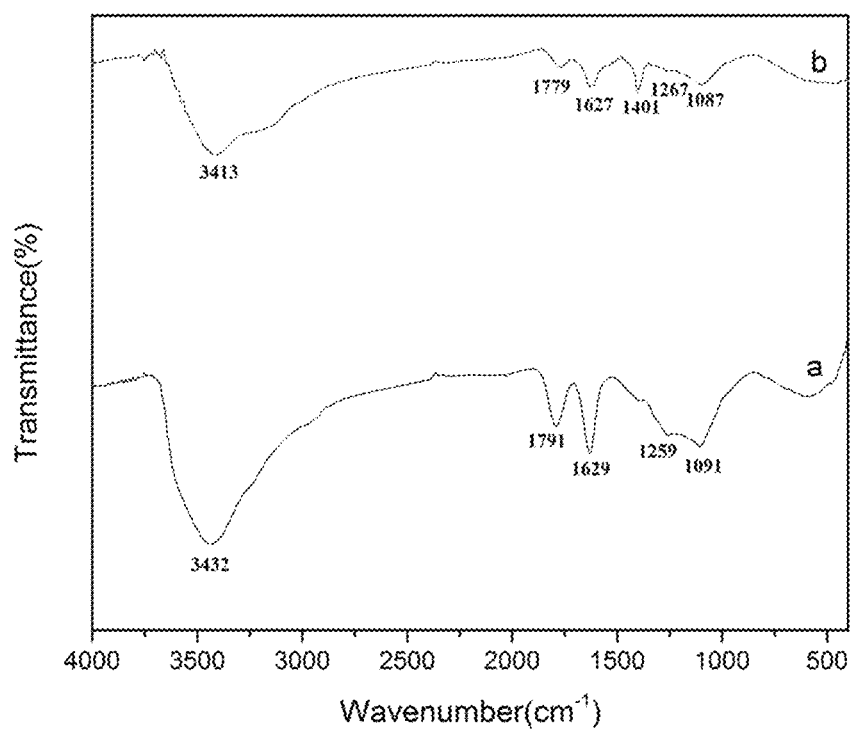
FIG. 2 shows a FTIR spectra of purified Nanodiamond (a), and aminated Nanodiamond (b) of example 3.

FIG. 2 shows a FTIR spectrum of the Nanodiamond sample prepared in example 1 purified (a) and after amination (b).

It can be seen from the FTIR spectrogram that carboxyl groups are attached to the surface of the purified Nanodiamond. The broad absorption peak near 3432 $cm^{-1}$ in the figure is —OH stretching vibration absorption peak, and the absorption peak near 1629 $cm^{-1}$ is —OH bending vibration absorption peak, —COOH stretching vibration absorption peak near 1791 $cm^{-1}$, which indicates that carboxyl and hydroxyl groups are attached to the surface of the oxidized Nanodiamond. The C—O—C antisymmetric stretching vibration peak appears near 1259 $cm^{-1}$. In the spectrum after amination modification, the broad absorption peak near 3413 $cm^{-1}$ is a stretching vibration peak of —NH, and the new absorption peak appearing at 1401 $cm^{-1}$ is a stretching vibration peak of —C—N. This characteristic peak indicates that the surface of Nanodiamond modified by ball milling is bonded with amino groups. Comparing the graphs of a and b, the carbonyl stretching vibration peak of Nanodiamonds after amination modification is red-shifted from 1791 $cm^{-1}$ to around 1779 $cm^{-1}$, which also indicates that Nanodiamonds can be efficiently functionalized by ball milling amine. The modified Nanodiamond is successfully obtained.

TABLE 1

Infrared spectrum analysis

| FTIR PEAK WAVE NUMBER/CM$^{-1}$ | CORRESPONDING VIBRATION PEAK |
|---|---|
| 3413 | a stretching vibration peak of NH |
| 1791 | a stretching vibration absorption peak of C=O |
| 1629 | a bending vibration absorption peak of OH |
| 1401 | a stretching vibration peak of C—N |

Figure 3:
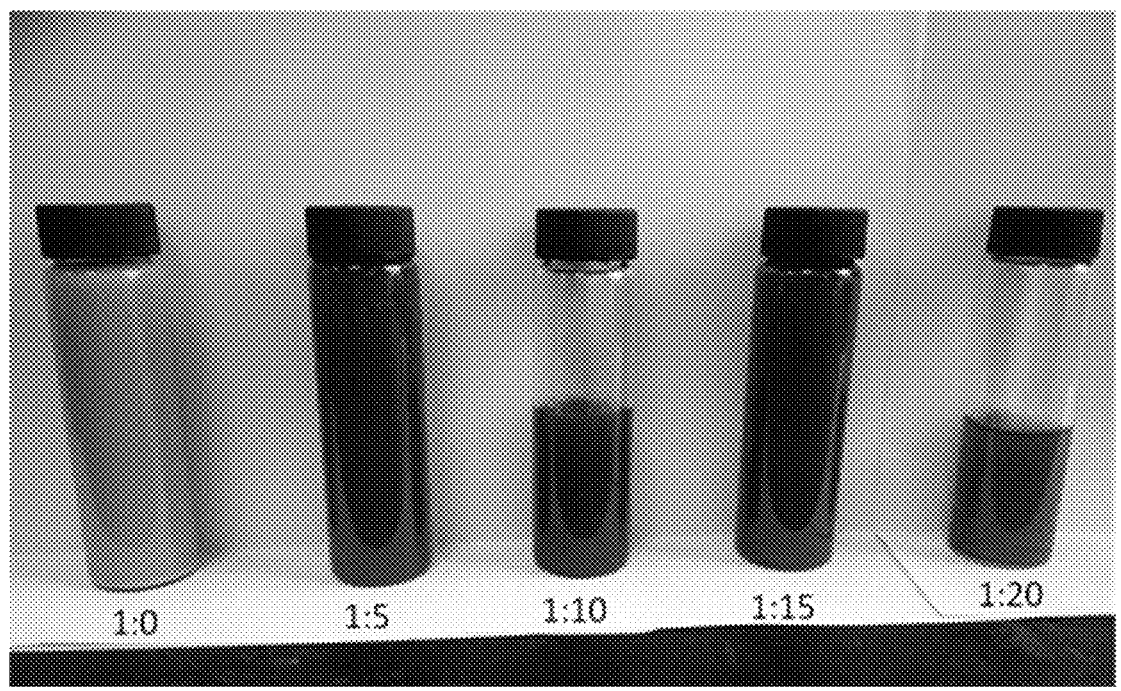
FIG. 3 shows a photo of Nanodiamond colloid solution in different amination reagent ratio conditions of example 1 to 5.

FIG. 3 shows a photo of Nanodiamond colloid solution in different amination reagent ratio conditions of example 1 to 5. FIG. 4 shows a particle size distribution of Nanodiamond colloid solution in different amination reagent ratio (The mass ratio of Nanodiamond to ammonium chloride) conditions of example 1 to 5. It can be observed that while the mass ratio of amination reagent to Nanodiamond is 1:0, the dispersion effect of Nanodiamond is poor, and the aqueous solution is an emulsion with an average particle size of 516 nm. After adding aminated modified particles, the Nanodiamond dispersion effect is better. While the amount of amination reagent increased from 1:5 to 1:10, the smallest particle size of Nanodiamonds reached 43.4 nm. The surface of the aminated Nanodiamond has more hydrophilic groups, which improves the dispersibility of the Nanodiamond in deionized water; the immobilization of the amino group on the surface of the Nanodiamond can enhance the stability of the system. Therefore, the modified Nanodiamond can be stored stably for a long time.

Figure 5:
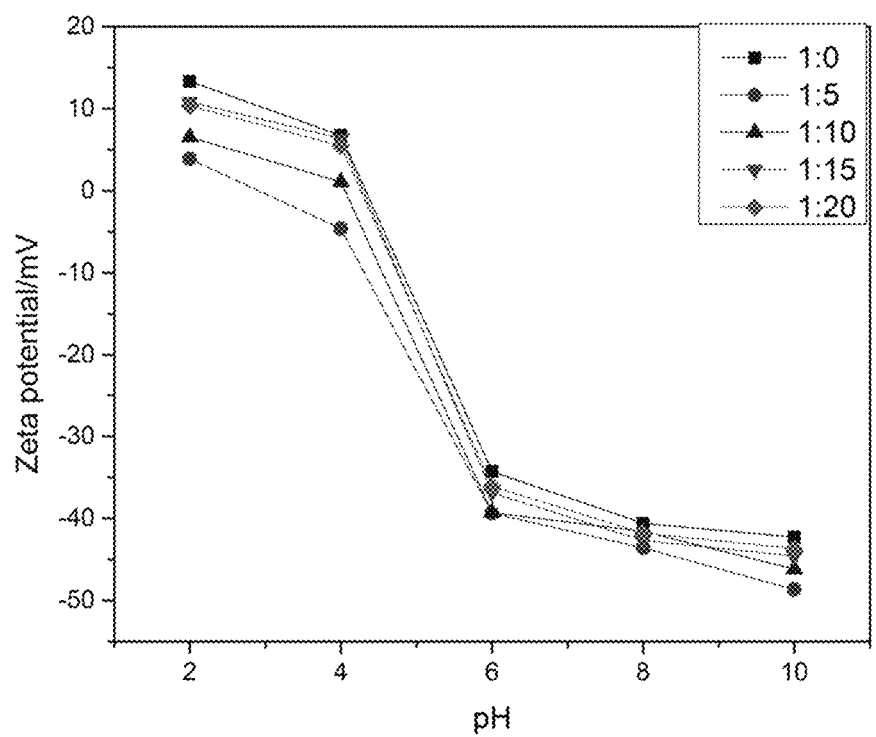
FIG. 5 shows a Zeta potential-pH graph of Nanodiamond colloid solution in different amination reagent ratio conditions of example 1 to 5.

FIG. 5 shows a Zeta potential-pH graph of Nanodiamond colloid solution in different amination reagent ratio conditions of example 1 to 5. It can be observed that while the ratio of amination reagent is 1:10, the degree of potential decrease is the most significant. The isoelectric point appears around pH=3. The potential value corresponding to different pH is the smallest. While pH=10, the minimum zeta potential is −49.9 mV. While the ratio of aminating reagent increases from 1:0 to 1:10, the corresponding lower potential value of each pH decreases, and while the ratio of aminating reagent increases to 1:20, the corresponding potential value of each pH value increases. These indicate that more hydrophilic groups are attached to the surface of Nanodiamonds after amination modification, and the particles have greater electrostatic repulsion, so as to achieve the dispersion effect.

Figure 6:
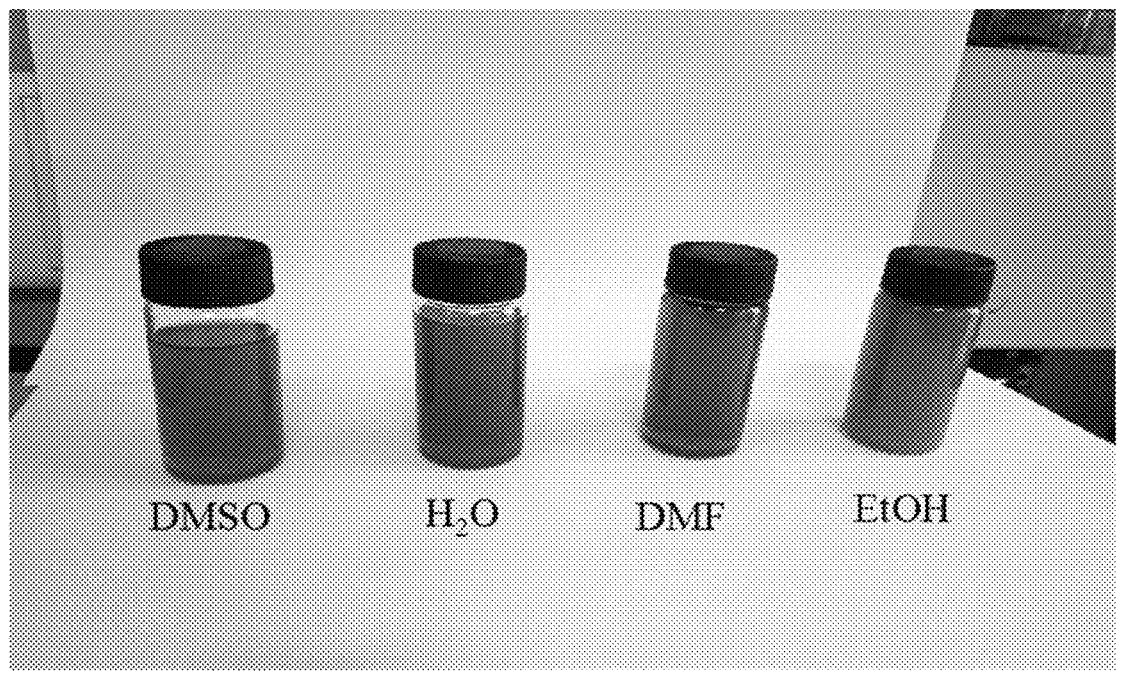
FIG. 6 shows a photo of colloid solution of aminated Nanodiamond prepared in example 3 for secondary dispersion in different solvents.

FIG. 6 shows a photo of the colloid solution of aminated nanodiamond prepared in example 1 for secondary dispersion in different solvents. It can be seen that after amination modification, Nanodiamonds are dispersed in aqueous phase to obtain colloid solution, and Nanodiamond particles are obtained after the colloid solution is dried. The particles can be dispersed again in the solvent to form colloids with an ultrasonic, such as deionized water, DMSO, ethanol, DMF, etc. DLS test results show that the average particle size of Nanodiamonds has little change and can be stored stably for a long time, so it can be widely used in drug carriers, thermal interface materials, photoelectric materials, and lubricating materials. Experimental conditions: grinding for 2 hours, grinding media ratio of 1:5, grinding material ratio of 1:10, grinding aid ratio (NaCl) of 1:5.

FIG. 7 shows a particle size distribution of the colloid solution of aminated Nanodiamond prepared in example 3 for secondary dispersion in different solvents. FIG. 8 shows a TEM images of aminated Nanodiamond prepared in example 3. It can be seen that the Nanodiamond modified by amination can be dispersed in deionized water, ethanol, DMSO, and DMF again, and present colloid state. The analysis of the DLS results show that a average particle size of the re-dispersed water is 48.9 nm, 53.6 nm in ethanol, 58.4 nm in DMSO, and 68.7 nm in DMF. All particle sizes are below 100 nm, indicating that the aminated modified Nanodiamonds have better re-dispersion effect.

Example 6 Application of the Aminated Nanodiamonds Prepared in Example 1 as Fluorescent Probes in Cellular Biomarking 1, Cell culture and labeling (1) Five types of cells were respectively seeded on a six-well cell culture plate, the cell density in each well: $5 \times 10^5 \pm 0.05 \times 10^5$ cells, cultured in an incubator with 37° C., 5% $CO_2$ for 24 hours. According to three different dyeing times required by the experiment, two parallel experiments were set up for each dyeing time.

(2) A mixed dye solution of aminated Nanodiamond and culture medium was prepared, and a concentration of aminated Nanodiamond was 1 mg/ml.

(3) The cultured six-well cell culture plate was taken out, the medium in it was aspirated and discarded, and 3 ml of the mixed solution was added to each well for cell staining. Continue to cultivate.

2, Collect cell marker pictures (1) After adding the aminated Nanodiamond mixture, the mixture was sucked out at 5 min, 15 min, and 30 min.

(2) After that, the cells were washed with PBS for three times, and 1 ml of fresh medium was added to each well of the six-well cell culture plate.

(3) Observed with microscope, the pictures of bright field and fluorescence field in the same field of view were collected separately.

3, FIG. 9A-E shows a real-time photographs of aminated Nanodiamond entering living cells. Comparing the fluorescence intensity of the real-time taken pictures of aminated Nanodiamond staining for 30 minutes with the previous outside of the cell, it can be found that the fluorescence intensity of the aminated Nanodiamond particles is relatively weak before entering the cell, but the intensity is increased in the real-time taken picture. The reason may be that the density of aminated Nanodiamonds increased after entering the cells, and the aggregation effect is achieved in the cells, the intracellular vibration is restricted, the radiation attenuation ratio increased, and the fluorescence intensity increased. Therefore, aminated Nanodiamonds can be used as fluorescent probes to label cells.

Although the aminated Nanodiamond have fluorescence intensity, its intensity is not obvious. After the aminated Nanodiamond enters the cell, since the surface of the aminated Nanodiamond particle is attached with many amino functional groups, as the cell absorbs the particles, the distance between the particles in the cell will gradually decrease to form many hydrogen bonds. Because the structure of aminated Nanodiamonds is relatively stable, it did not perform intramolecular motion and rotation like ordinary organic molecules to release energy to return the molecules to steady state, but may release energy in weak vibration mode. However, the higher energy released by the vibration mode is suppressed due to the formation of hydrogen bonds, making it return to steady state. Energy release in the form of light energy is increased, and fluorescence intensity is increased.

What is claimed is:

1. A method for preparing a monodisperse aminated Nanodiamond colloid solution, comprising steps of:

mixing a purified Nanodiamond powder of appropriate particle size with ammonium chloride and sodium chloride in a reasonable mass ratio at room temperature, placing in a ball mill for dry ball milling, washing with deionized water, dispersing with ultrasonic, and centrifuging to obtain monodisperse amine Nanodiamond black colloid solution.

2. The method for preparing a monodisperse aminated Nanodiamond colloid solution according to claim 1, wherein the appropriate particle size of the purified Nanodiamond powder is in a range of 30 nm- 100 µm.

3. The method for preparing a monodisperse aminated Nanodiamond colloid solution according to claim 1, wherein the reasonable mass ratio of the purified Nanodiamond to deionized water is in a range of 1:20-2000, the reasonable mass ratio of ammonium chloride and sodium chloride is in a range of 1:2-100.

4. The method for preparing a monodisperse aminated Nanodiamond colloid solution according to claim 1, wherein the reasonable mass ratio of the purified Nanodiamond powder to the ammonium chloride is in a range of 1:0.1-100.

5. The method for preparing a monodisperse aminated Nanodiamond colloid solution according to claim 1, wherein adding ball milling beads in a ball milling process, the ball milling beads are non-metallic ball milling beads, including but not limited to agate, corundum, zirconia, and silica.

* * * * *